United States Patent [19]

Trauner et al.

[11] Patent Number: 5,368,841
[45] Date of Patent: Nov. 29, 1994

[54] PHOTODYNAMIC THERAPY FOR THE DESTRUCTION OF THE SYNOVIUM IN THE TREATMENT OF RHEUMATOID ARTHRITIS AND THE INFLAMMATORY ARTHRITIDES

[75] Inventors: Kenneth Trauner, Sacramento, Calif.; Tayyaba Hasan, Arlington, Mass.

[73] Assignee: The General Hospital Corporation, Boston, Mass.

[21] Appl. No.: 16,609

[22] Filed: Feb. 11, 1993

[51] Int. Cl.$^5$ ............... A61K 49/00; A61K 31/33
[52] U.S. Cl. ............................... 424/9; 514/183; 514/825; 540/145
[58] Field of Search ............ 514/183, 185, 410; 540/145; 424/9

[56] References Cited

U.S. PATENT DOCUMENTS

| | | | |
|---|---|---|---|
| 4,758,429 | 7/1988 | Gordon | 424/85 |
| 4,849,207 | 7/1989 | Sakata | 424/1.1 |
| 4,877,872 | 10/1989 | Morgan et al. | 540/145 |
| 4,996,233 | 2/1991 | Horrobin | 514/560 |
| 5,028,594 | 7/1991 | Carson | 514/23 |
| 5,079,262 | 1/1992 | Kennedy et al. | 514/561 |
| 5,238,940 | 8/1993 | Liu et al. | 514/410 |

OTHER PUBLICATIONS

Dougherty et al., Photodynamic Theraphy for the Treatment of Cancer: Current Status and Advances, In Photodyanmic Therapy of Neoplastic Disease, Kessel ed., (CRC Press, Boca Raton, Fla.) vol. 1, pp. 2–19, 1989.

Sledge et al., Intra-articular Radiation Synovectomy, Clinical Orthopaedics and Related Research 182:37–40, 1984.

Zuckerman et al., Treatment of Antigen-induced Arthritis in Rabbits with Dysprosium 165-Ferric Hydroxide Macroaggregates, J. Orthopaedic Research 7:50–60, 1989.

Primary Examiner—Marianne M. Cintins
Assistant Examiner—T. J. Criares
Attorney, Agent, or Firm—Fish & Richardson

[57] ABSTRACT

A method of treating proliferative diseases of the synovial joint using photodynamic therapy. In particular the method of the invention may be used to destroy synovial tissue in inflammatory joint conditions associated with diseases such as rheumatoid arthritis, lupus erythematosus and other rheumatoid variants. A number of methods of delivery are provided, some of which are non invasive.

16 Claims, 5 Drawing Sheets

PHOTODYNAMIC THERAPY FOR THE DESTRUCTION OF THE SYNOVIUM IN THE TREATMENT OF RHEUMATOID ARTHRITIS AND THE INFLAMMATORY ARTHRITIDES

STATEMENT AS TO FEDERALLY SPONSORED RESEARCH

Funding for the work described herein was provided by the Federal Government Office of Naval Research Grant No. N0001491C0084. The federal government has certain rights to the invention.

BACKGROUND OF THE INVENTION

The invention relates to the use of photodynamic therapy for the destruction of diseased synovium.

Photodynamic therapy generally refers to an experimental cancer treatment modality that selectively kills cancer cells by an interaction between absorbed light an a retained photoactivatable agent (Kessel, Photochem. Photobiol. 44:489–493; Bottiroli et al., Photochem. Photobiol. 47:209–214, 1988; Salet et al., Photochem. Photobiol. 53:391–3, 1991; Gross, *Photobiological Techniques* (chapter 9), Valenzeno et al. eds., Plenum Press, New York, 1991; Star et al., Photochem and Photobiol, B: Biology 1:149–167, 1987; and Jori et al., *Photodynamic Therapy of Neoplastic Disease*, Kessel ed., CRC Press, Boca Raton, Fla., 1989). Chemical sensitization of live tissues by light was first reported in 1900 by Raab. Uptake of hematoporphyrin derivative (HPD) in neoplastic tissue was first described by Auler and Banzer (Z. Krebforsch 53:65–68, 1942). Uptake was later confirmed by fluorescence by Figge et al (Proc. Soc. Exp. Biol. Med. 68:640–641, 1948). Lipson et al. demonstrated tumor localization of HPD in 1960 (JNCI 26:1–12, 1961).

The HPD semipurified mixture of porphyrins was later further purified to a combination of esters and ethers of dihematoporphyrin (DHE). The formulation predominantly in use is marketed as Photofrin® and HPD/Photofrin® was the first FDA approved photosensitizing agent available for PDT trials. Photofrin® has subsequently been tested extensively for the destruction of multiple tumors in numerous medical disciplines (Dougherty et al., *In Photodynamic Therapy of Neoplastic Disease*, Kessel ed., CRC Press, Boca Raton, Fla., 1989).

The mechanism of action for hematoporphyrin derivatives such as Photofrin® in the treatment of neoplastic disease is well delineated. For the porphyrins, large molecular aggregates accumulate around tumor neovasculature. Poor lymphatic drainage of neoplastic tissues may be the cause of retarded clearance times from these tissues. Once sequestered, the molecular aggregates dissociate, and the hydrophobic components partition Photofrin® into cell membranes. The primary cellular sites of photodynamic activity are thought to be cellular and mitochondrial membranes. Nucleic acids and proteins are also damaged by photooxidation (Henderson et al., *Porphyrin Localization and Treatment of Tumors*, Doiron and Gomer eds., Liss, New York, 1984, pp. 601–612).

Initiation of photodynamic activity is caused by excitation of the sensitizer by light that falls within its absorption band. The wavelength specificity is dependent on the molecular structure of the photosensitizer, where a greater degree of conjugation within a molecule leads to greater absorbance at longer wavelengths. Activation of photosensitizers occurs with sub-ablative light fluences. Toxicity is achieved by $O_2$ radical toxicity. The singlet $O_2$ reacts with double bonds, and organoperoxides. These, in turn, initiate free radical chain reactions which degrade and disorganize membranes, uncouple oxidative phosphorylation and lead to cellular disruption (Jori et al., *Photodynamic Therapy Of Neoplastic Disease*, Kessel ed., CRC Press, Boca Raton, Fla., 1989; and Weishaupt et al., Cancer Res 36:2326–2329, 1976).

Several characteristics of photodynamic therapy allow for the selective destruction of diseased tissue without damage to non-pathological tissue (Kessel, Photochem. Photobiol. 44:489–493; Bottiroli et al., Photochem. Photobiol 47:209–214, 1988; Salet et al., Photochem. Photobiol. 53:391–3, 1991; Gross, *Photobiological Techniques* (chapter 9), Valenzeno et al. eds., Plenum Press, New York, 1991; Star et al., Photochem and Photobiol, B: Biology 1:149–167, 1987; Jori et al., *Photodynamic Therapy of Neoplastic Disease*, Kessel ed., CRC Press, Boca Raton, Fla., 1989; Dougherty et al., *In Photodynamic Therapy of Neoplastic Disease*, Kessel ed., CRC Press, Boca Raton, Fla., 1989; Richelli et al., J. Photochem Photobiol 6:69–77, 1990; and Jori and Spikes, J. Photochem Photobiol. 6:93–101, 1990; Mazierre et al., J. Photochem Photobiol. 6:61–68, 1990; Brault, J. Photochem and Photobiol 6:79–86, 1990; and Pottier, J. Photochem Photobiol. 6:103–109, 1990). Photosensitizing agents are non-toxic until activated by specific frequencies and dosages of light energy. In addition, photosensitizers may be activated when transient differences in uptake occur between pathological and normal tissues. Differences in both temporal and geographic biodistribution in tissues may be taken advantage of for selective destruction of pathological tissue.

Carson, U.S. Pat. No. 5,028,594 describes a method for the selective elimination of hematopoietic cells involved in rheumatoid arthritis by use of photactivatable cytotoxic agents in combination with light. The photoactivated agents are tagged with ligands such as sugars, which target lymphocyte cells. In the example, monoethylenediamine monamide was administered to rats in combination with light, bringing about a reduction in joint swelling and inflammation.

Kennedy, U.S. Pat. No. 5,079,262 describes a method of detecting and treating tissue abnormalities such as skin lesions and tumors by the administration of aminolevulinic acid in combination with photoactivating light. Kennedy suggests the use of ALA, a metabolic precursor of protoporphyrin IX in a variety of PDT applications.

Attempts at destroying diseased synovium with nonselective toxic compounds have been unsuccessful (Goldberg et al, Arthritis Rheum. 19:737, 1976; Mitchell et al., JBJS 55-B:814, 1973; and Oka et al., Acta Rheum Scand 15:35, 1969). Most recently, in an effort to develop minimally invasive techniques, synovectomies have been performed with radioactive compounds (Zuckerman et al., J. Orthop Res. 7:50–60, 1989 and Sledge et al., Clin Orthop Rel Res 182:37–40, 1984). Although success has been achieved to a small degree, the use of radioactivity precludes widespread use.

SUMMARY OF THE INVENTION

The invention features a method of treating a proliferative inflammatory joint disease in a patient. The joint disease is treated by administering a photoactivatable cytotoxic compound or precursor thereof followed by the administration of photoactivatable lightwaves to the region of the diseased synovial tissue. Using this method the synovial tissues are destroyed.

Diseases of the joint which may be treated using PDT are listed in part in Table 1. In addition to those diseases specifically listed, it is understood that any disease which involves proliferation of the synovial tissues may be treated using the methods of the invention.

Compounds are administered to a patient using guidelines for administration which will produce greater concentrations of the drugs in the target tissues relative to the surrounding tissue, while maintaining adequate levels of the drug in the target. In general, this differential drug localization can be achieved using guidelines for administration determined using standard techniques known in the field of pharmacology for determining a drug clearance time course. The ratio of drug in the affected tissue to drug in the surrounding tissue is preferably 2:1 or greater. Specifically, compounds may be administered either systemically or locally to the area of the joint.

Systemically or locally administered compounds which are useful in the invention are those which are taken up in greater amounts and/or retained substantially longer in the pathogenic tissues relative to the surrounding tissues of a patient. Compounds with this characteristic can be defined as those which have a useful therapeutic index for photodynamic therapy induced cell killing of the synovium of at least 50. In addition, useful compounds preferably have a therapeutic ratio for photodynamic therapy induced synovial cell killing of at least 10. The therapeutic index is defined by the ratio of the toxicity of compound and the addition of light: toxicity of compound alone. The therapeutic ratio is defined as the toxicity of the compound with the addition of light in diseased tissue: toxicity of the compound with the addition of light in normal tissue. Toxicity is defined as cell death.

Specific photoactivatable drugs which may be used to treat diseases of the joint are summarized, in part, in table 2. Because of the nature of vascularization of proliferating synovial tissue any systemically non-toxic photoactivating compound or precursor thereof which is useful for photodynamic therapy of neoplasias may generally be useful in the methods of the invention. This is illustrated in the examples, below. Preferably, Photofrin ® (hematoporphyrin derivative, Photofrin ®I and photofrin ®II), benzoporphrin derivatives and/or aminolevulinic acid are administered as a part of the invention.

Light of the appropriate wavelength for a given compound may be administered by a variety of methods known to one skilled in the art. These methods may involve laser, nonlaser, or broad band light and may result in either extracorporeal or intraarticular generation of the light of the appropriate wavelengths. Light used in the invention may be administered using any devices which generates the appropriate wave form including but not limited to fiber optic instruments, arthroscopic instruments or instruments which provide transillumination.

This method of photodynamic therapy will allow for a minimally invasive technique for destroying diseased synovium without damage to healthy intra-articular tissues.

Other features and advantages of the invention will be apparent from the following description and from the claims.

BRIEF DESCRIPTION OF THE DRAWING

The drawings will first be briefly described.

Drawings

DESCRIPTION OF THE PREFERRED EMBODIMENTS

Rheumatoid arthritis is a disease characterized by proliferative erosive synovial tissue which destroys intraarticular and periarticular tissues. For patients failing medical management through pharmaceutical administration open surgical synovectomy or more aggressive procedures such as joint replacement have been the only treatment options. Photodynamic therapy synovectomy now offers an effective, less invasive new therapeutic alternative. Photoactive chemicals are injected into diseased joints either locally or systemically. The local joint region is then exposed to light via optical fibers threaded through small gauge hypodermic needles or, alternatively, the light source may also be provided extracorporeally by trans illumination. This treatment destroys the diseased synovium and potentially benefits the large population of patients for whom surgery is poorly indicated.

Figure 1:
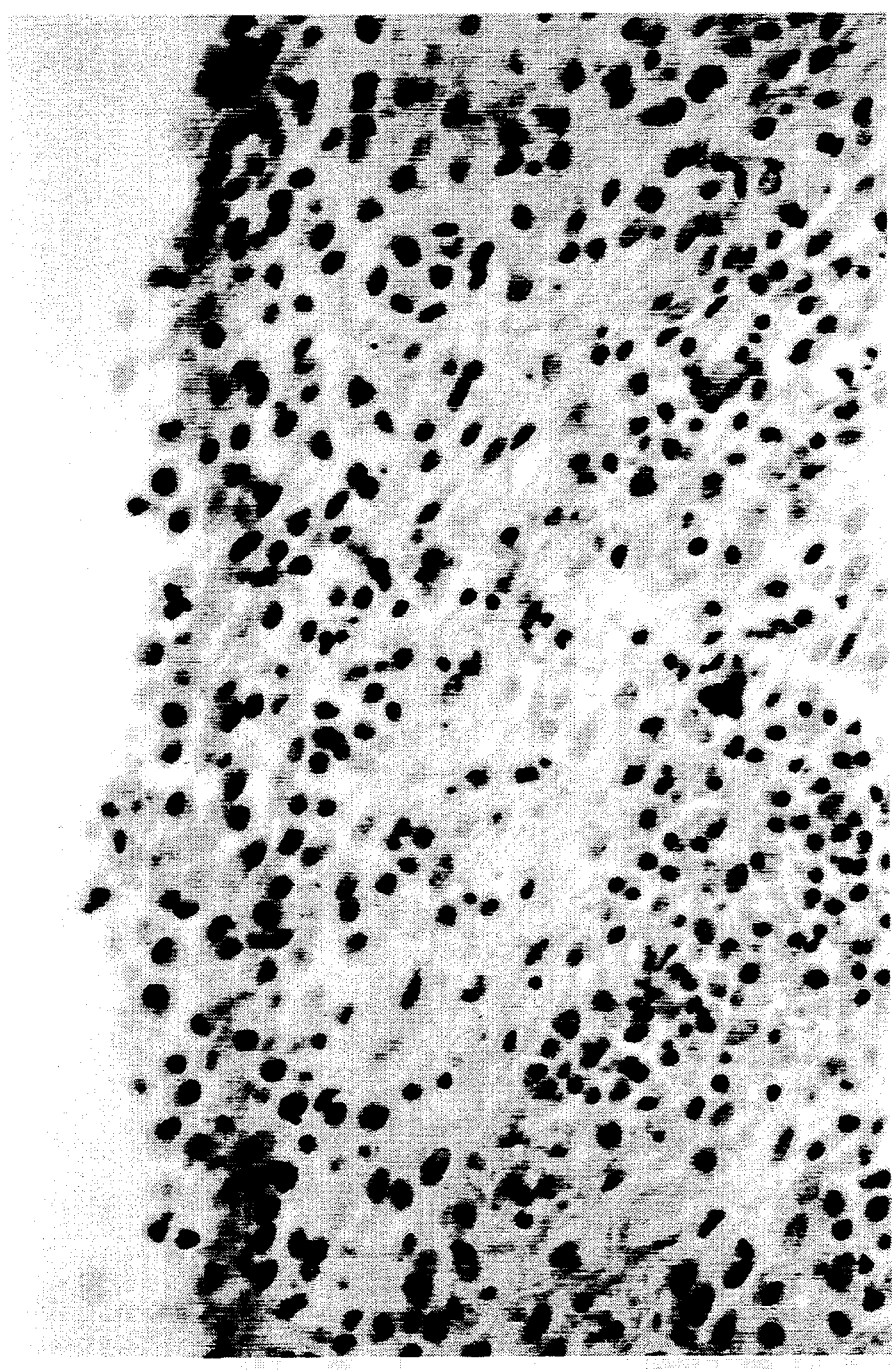
FIG. 1 is a photograph of the synovial tissue of the knee from a rabbit 11 weeks following initial skin sensitization according to the antigen induced arthritis protocol, 5 weeks after knee joint challenge with the antigen with no photodynamic therapy applied to the joint.
Figure 2:
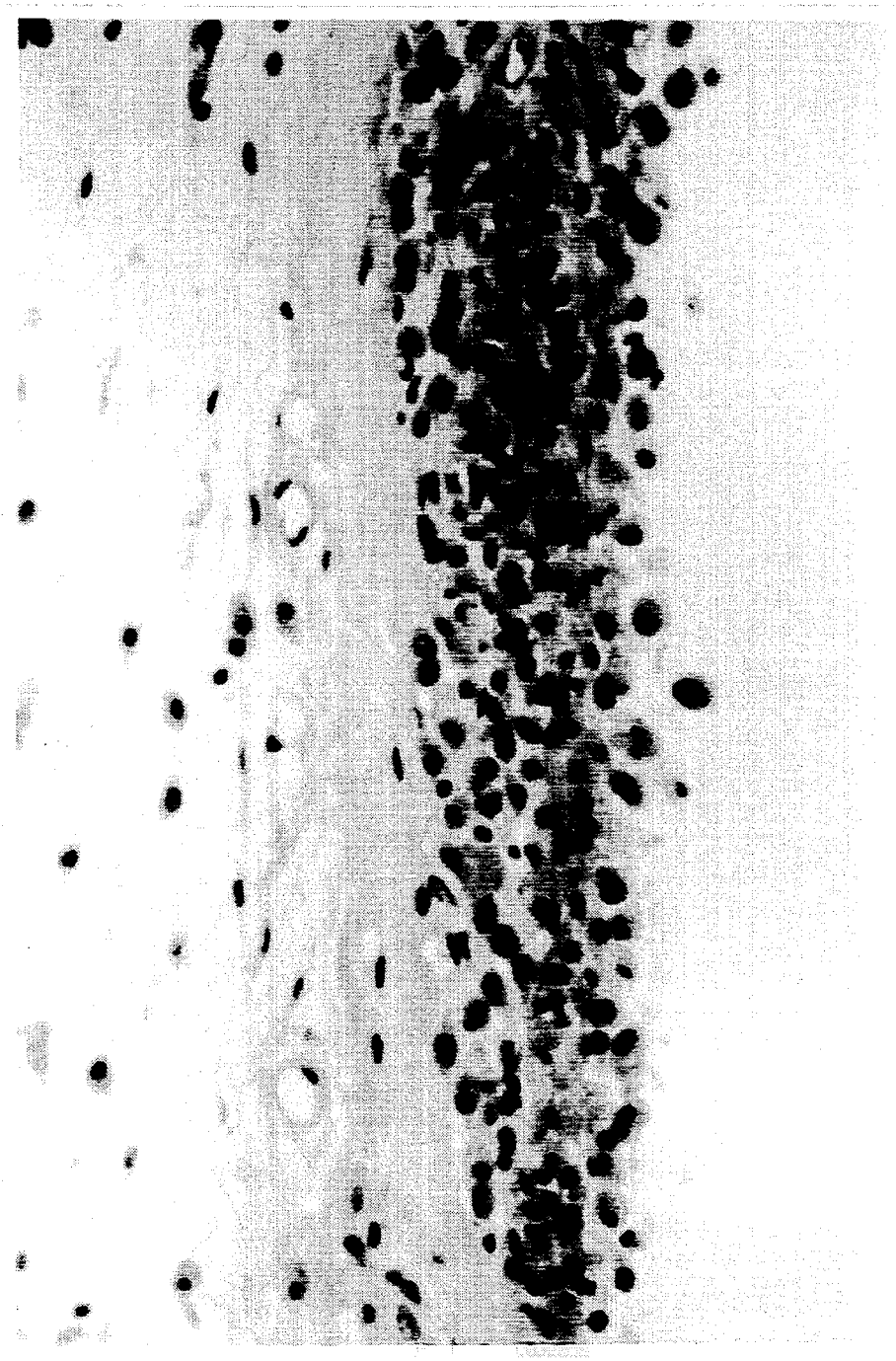
FIG. 2 is a photograph of the synovial tissue of the knee from a rabbit 11 weeks following initial skin sensitization according to the antigen induced arthritis protocol, 5 weeks after knee joint challange with the antigen, and 4 weeks after photodynamic treatment with Photofrin ® and light.

Examples A–D, below, demonstrate that photoactivatable chemicals localize selectively to the diseased synovium and are, therefore, promising for the treatment of the arthritic diseases. Photofrin ® which is a mixture of hematoporphyrins and is the most widely used of the anti-neoplastic photosensitizing agents has been investigated most thoroughly for its therapeutic promise. In one example, Photofrin ®, is demonstrated to be effective for the treatment of antigen induced arthritis. Biodistribution studies performed have documented that Photofrin ® is selectively taken up in synovium at 24 and 48 hours post systemic injection. Results demonstrating destruction of synovium without significant side effects indicate that photochemical synovectomy is an effective new treatment for rheumatoid arthritis (FIGS. 1 and 2).

Photofrin ® is but one example of a photoactivatable therapeutic which is an aspect of the invention. Its characteristics are illustrative of the localization and clearance characteristics of many other photodynamic compounds. Example A, below, illustrates that Photofrin ® localizes to the diseased proliferating synovial tissues. Example A below, indicates that Photofrin ® kills cells in the diseased synovium. Examples C and D indicate that this is a general effect with photodynamic compounds and their precursors when they come into contact with diseased synovium.

Numerous possibilities exist for delivery of both photosensitizing agents and light energy to the joints. Determining the most appropriate parameters for any photodynamic compound to be used for the treatment of arthritis may be done using the experimental techniques provide herein.

I. Delivery of Photoactivating Light

Newer photosensitizing compounds without systemic skin photosensitivity effects, activated in the near infrared and longer wavelength visible spectrum allow for light activation. This may be done via joint transillumination. Optical fibers may be passed via arthroscopes with direct visual targeting and activation of the compounds. Optical fibers may also be passed directly via small gauge hypodermic needles. Light may also be passed via percutaneous instrumentation using optical fibers or cannulated waveguides. Transillumination may be performed using a variety of devices involving laser or non-laser sources, i.e. lightboxes or convergent light beams. Activation may also be performed by open arthrotomy. Development of these parameters allows for minimally invasive, or non invasive means (via transillumination) for performing photodynamic synovectomies.

II. Delivery of Photodynamic Compounds

Local injection of the therapeutic chemical into joints may eliminate the need for systemic injection. The use of localized versus systemic injection is determined, in part, by the number of joints to be treated during a given therapeutic regime.

The therapeutic compounds to be administered for use in photodynamic therapy can be formulated for pharmaceutical or veterinary use by combination with an acceptable diluent, carrier or excipient and/or in unit dosage form. In using the therapeutic compounds in the methods of the invention, conventional pharmaceutical or veterinary practice may be employed to provide suitable formulations or compositions.

Thus, the formulations of this invention can be applied to parenteral administration, for example, intravenous, intraarticular, subcutaneous, intramuscular, intraventricular, intracapsular, intraspinal, intraperitoneal, topical, intranasal, aerosol, scarification, and also oral, buccal, rectal or vaginal administration.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences." Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, liposomes, and antibody conjugates. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The present factors can be used as the sole active agents or can be used in combination with other active ingredients.

The concentration of the present factors in the formulations of the invention will vary depending upon a number of issues, including the dosage to be administered, and the route of administration.

In general terms, the factors of this invention may be provided in an aqueous physiological buffer solution containing about 0.1 to 10% w/v compound for parenteral administration. General dose ranges are from about 0.2 mg/kg to about 1 g/kg of body weight per day; a preferred dose range is from about 0.1 mg/kg to 2 mg/kg of body weight per day. The preferred dosage to be administered is likely to depend upon the type and extent of progression of the joint condition being addressed, the overall health of the patient, the make up of the formulation, and the route of administration.

III. Method of Screening Therapeutics for Use in PDT if Arthritis

A. Development Antigen Induced Arthritis Rabbit

The following is a protocol which may be used to generate antigen induced arthritis in rabbits. Rabbits prepared in the manner can then be used to screen various phototherapeutics for their application to the treatment of arthritic disorders.

Protocol: 200 mg ovalbumin is weighed and dissolved in 10 ml normal saline and filtered through a millipore filter into a sterile beaker. Ovalbumin solution is then drawn into a sterile 20–30 cc glass syringe. In addition, 10 ml of Freund's adjuvant is drawn into another sterile glass syringe. Using a sterile metal 3 way stopcock, the two solutions are mixed by transferring them back and forth between syringes until solution is thick and white. The suspension is then transferred to sterile vials or sterile 25 ml erlenmeyer flasks with rubber stoppers. 0.2 ml of this sensitization solution is then injected via a 23 or 25 gauge needle into 5 areas in the back of each rabbit. Sensitization is repeated 3 weeks after initial immunization.

Joint challenge: 10 mg/ml ovalbumin is added to normal saline followed by millipore filtration into a sterile vial. Rabbits are anesthetized and their knees shaved. 0.25 ml of challenge solution is injected directly into the knee joint.

Using this technique monoarticular synovitis is achieved within 4 days and continues over two weeks. Animals left up to six months will exhibit cartilage erosion, occasional osteophyte formation and synovial infiltration.

B. Animal Studies of Photodynamic Therapeutics Using Rabbits with Antigen Induced Arthritis New Zealand white rabbits weighing 3–4 kg are divided into 3 groups as summarized in Table 3. All animals then undergo a six week sensitization period according to the Antigen Induced Arthritis Rabbit protocol. Bilateral knee joints of all animals are challenged at 60 days with intra-articular injections of 0.25 ml ovalbumin solution with a concentration of 2.5 mg/ml. Injections require sedation with rompen and ketamine. Six days post challenge, 24 animals in group A will receive a systemic injection of 2 mg/kg of the therapeutic to be tested in compound solution via 25 gauge needle into an ear vein. 16 animals in group B will serve as controls and not receive injections of the therapeutic agent. Localized injection may also be used 48 hours post compound injection, or at any other time indicated by drug clearance studies. Animals in groups A and C will are again sedated with rompen and ketamine. Bilateral knees of all animals in group A and the right knee of animals in group C will receive light activation treatments. 400 nm–690 nm wavelength light energy, or any wave length which is activating for the chosen therapeutic, will be transmitted via 400 micron optical fiber through a 23 gauge needle into the knee joint cavities. Alternatively, light may be applied extracorporeally. A total light energy of 100J/cm2, or that energy range deemed appropriate for a given compound, will be applied to each joint over 20 minutes with an average laser power setting of 3–5 watts, or that wattage and time which is effective for a given compound. 6 animals from group A and 4 animals from both group B and group C are sacrificed at one week, two weeks, four weeks and 10 weeks post compound injection. Gross observations at time of harvest are then recorded. Samples of synovium, articular cartilage, meniscus and tendon are harvested and fixed in formulin. Specimens and then imbedded in paraffin, sectioned and stained with hematoxylin and eosin. Specimens are then examined microscopically for inflammation, scarring and necrosis. This general schedule is summarized below. It is understood that specific modifications in dosage, timing, light wavelength and duration are made for each therapeutic compound tested. These general perimeters are know to those skilled in the art and are summarized, in part, in the following papers and references cited therein: Gomer, Photochemistry and Photobiology 54:1093–1107, 1991; Maziere et al., J. Photochem. Photobiol. B: Biol. 8:351–360, 1991; Allison et al., Photochemistry and Photobiology 54:709–715, 1991; Allison et al., SPIE Proc., In Press, 1991; Allison et al., Photochemistry and Photobiology 52:501–507, 1990; Poon et al., J. Neurosurg. 76:679–686, 1992; Reddi et al., Br. J. Cancer 61:407–411, 1990; Richter et al., Br. J. Cancer 63:87–93, 1990;

This protocol allows the practitioner to:

1) Document, with pathology, the ability of an activated photosensitizing agent to destroy synovium.

Samples of synovium from animals at all termination dates are fixed, imbedded in paraffin, stained and examined microscopically. Gross observations at time of harvest are to be noted. Knee inflammation at the time of light application will be examined clinically and recorded. Knee dissection observations will be recorded at time animals are sacrificed.

2) Document the non-deleterious effects of activated Photofrin ® on articular cartilage, meniscus and other periarticular tissues.

Samples of articular cartilage, meniscus, tendon and muscle from animals as all termination dates are fixed, imbedded in paraffin, stained and examined microscopically. Gross observations at time of harvest are noted. Knee dissection observations are recorded at time of tissue harvest.

The following examples are meant to illustrate not limit the invention.

IV. EXAMPLES

Four examples relating to photochemical synovectomy are provided.

The first study, Example A, is a biodistribution study performed with 30 rabbits (60 knees) 1) to reestablish the animal model after making modifications suggested by the pilot study; 2) to establish selective uptake of hematoporphyrin derivative, Photofrin ® (PF), in inflamed synovium; 3) to identify the temporal distribution of Photofrin ® in synovium to optimize future delivery of light energy for photochemical activation; 4) to quantify Photofrin ® uptake in synovium as a suggestion of feasibility in destruction of synovium; 5) to document biodistribution of Photofrin ® in articular cartilage, muscle and skin.

Example B was a study conducted with 12 animals 1) to establish the feasibility of using photodynamic therapy for the treatment of an inflammatory condition; 2) to establish the antigen induced arthritis rabbit model; 3) to identify potential sources of difficulty prior to proceeding with a larger scale animal study and 4) to establish our surgical approach and route of administration of light energy. These experiments were done with Photofrin ®.

Thirdly, Example C is a study presented which demonstrates that the phototherapeutic BPD is also localized effectively to the synovium allowing the generalization of results regarding issues of localization and clearance for other photodynamic compounds localized in neoplastic tissue but not yet demonstrated to specifically localize to synovial tissues.

The fourth study, Example D, demonstrates that aminovuulinic acid (ALA) may be administered as a precursor to yield the photosensitizer Protoporphyrin IX in situ in the synovium.

EXAMPLE A: BIODISTRIBUTION OF PHOTOFRIN ®

Methods

Thirty New Zealand White rabbits weighing 2–4 kg were sensitized over a six week period with two cutaneous injections of ovalbumin suspended in Fruends adjuvant. At six weeks, the knee joints of all animals were challenged with an intra-articular injection of ovalbumin solution. Seven days following joint challenge, 25 animals received systemic intravenous injections with Photofrin ® (2.0 mg/kg). Animals were killed at 6, 12, 24, 48 and 72 hours post Photofrin ® injection and tissue samples were obtained of skin, quadriceps muscle, knee synovium, articular cartilage, meniscus, bone and tendon. Tissue weight was measured (Mettler AE 163 balance) and tissue samples were frozen at −90 degrees C. (Revco Ultra Low Freezer) until dye extraction.

For extraction, tissue samples were homogenized (Homogenizer, Model PT 10/35, Brinkman Instruments, Co., Westbury, N.Y.) in 8 cc 0.1N NaOh solution. Each sample was centrifuged at 17,000 RPM (Sorvall RC-5B, refrigerated superspeed centrifuge, DuPont instruments) for 20 minutes. The fluorescence of 2 cc of supernatant was measured with a spectrofluorometer (Model Flourolog 2, Spex Industries, Inc., Edison, N.J.) and compared to that of standard solutions of Photofrin ® with known concentration, and Photofrin ® mixed with supernatant of extracted control quadriceps muscle. The excitation wavelength 366 nm and fluorescence spectrum between 600 and 700 nm was analyzed. Untreated animals will served as controls and for background correction.

Figure 3:
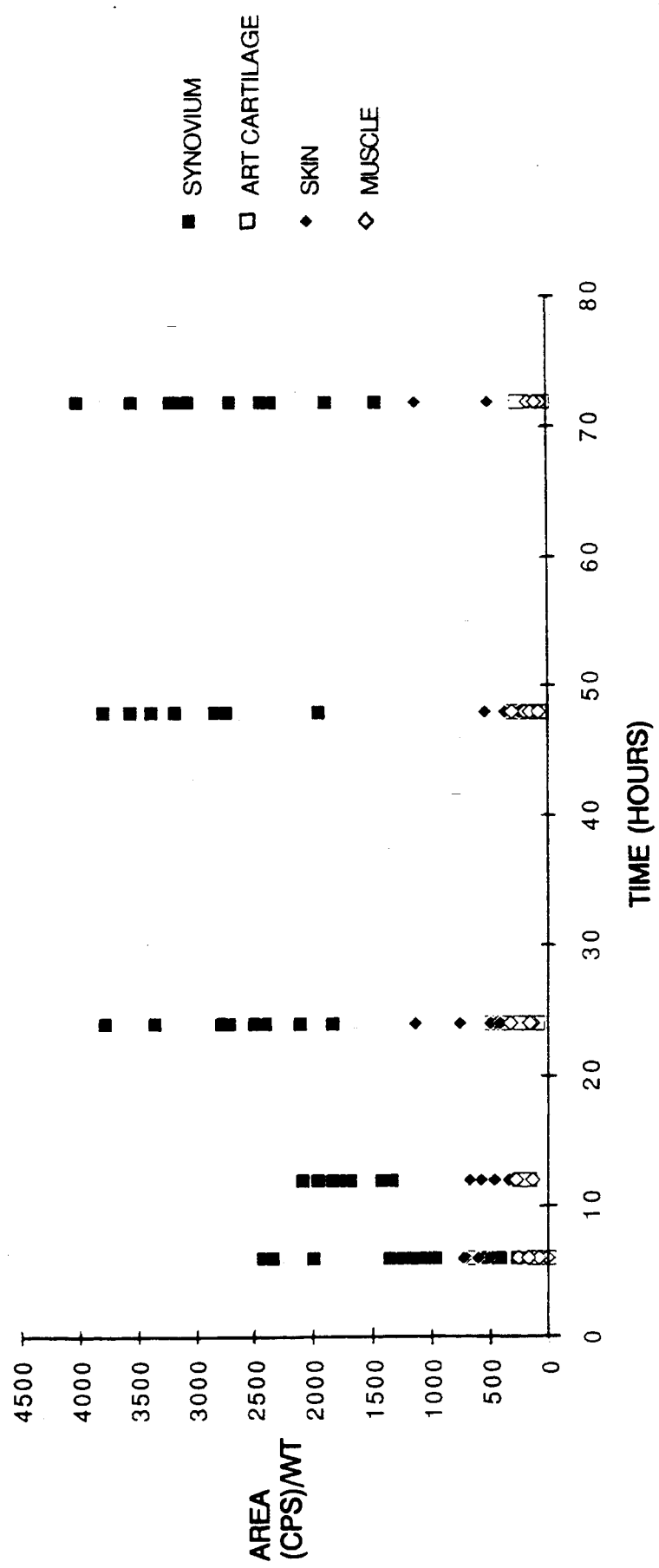
FIG. 3 is a graph of the biodistribution of Photofrin ® in the synovium, articular cartilage, skin, and muscle between 0–80 hours after administration.

The biodistribution of Photophrin ® within synovium, articular cartilage and meniscus was also studied with fluorescence microscopy. At each of the harvest intervals of 6, 12, 24, 48 and 72 hours post injection, tissue specimens were obtained from experimental and control animals. Samples were placed in O.C.T. medium and frozen at −90 C. Unstained frozen sections at 10 microns were prepared using a cryostat (Microm, Inc., Heidelberg, Germany) and analyzed with a fluorescence microscope (Axiophot, Zeiss, Oberkochen, Germany) under epiluminescence of a mercury lamp (HBO 200 W/2, Zeiss). The excitation wavelength was between 300 and 500 nm.; the emission above 580 nm was displayed on a video screen after light amplification in a silicon intensified tube video camera (MTI - DAGE SIT 66) and averaging of 60 images. The images were digitized and stored using a Macintosh II computer equipped with a digitizing board (DT 2255, Data Translation, Marlboro, Mass.) Frozen sections were compared to histological slides of the same area after staining with hematoxylin and eosin. Untreated animals served as controls. These results are summarized in FIG. 3.

Results

Light and Fluorescence Microscopy: Consistent inflammation of synovium was seen in all animals at the time the animals were killed. Samples of synovial tissue from control animals demonstrated no uptake by fluorescence microscopy. Uptake of Photofrin ® was not visualized in samples of articular cartilage and meniscus obtained from experimental animals. Synovial samples from experimental animals which had received systemic injections of Photofrin ® demonstrated significant uptake at 12, 24, 48 and 72 hours. Photofrin ® fluorescence exhibited a cellular pattern suggestive of synovial and inflammatory cellular uptake.

Quantitative spectroscopic analysis of extracted tissue samples again demonstrated significant inflamed synovial uptake of the Photofrin ®. Maximum uptake occurred at 48 hours post injection. Comparison with spectroscopic analysis of known sample concentrations revealed Photofrin ® concentrations of greater than 4 micrograms/gram of tissue. The dosage is comparable to therapeutic levels documented in successfully treated neoplastic tissues. Fluorescence levels in articular cartilage, meniscus and muscle was negligible and did no exceed baseline levels of endogenous porphyrin production.

Conclusion

This biodistribution study demonstrates selective uptake of hematoporphyrin derivative (Photofrin ®)) in inflamed synovium in a rabbit antigen induced arthritis model for rheumatoid arthritis. The study indicates that light activation of the knee joints at 48 hours after systemic Photofrin ® injection may be performed for the isolated destruction of inflamed synovium. Photofrin ® uptake in articular cartilage, meniscus, muscle and tendon appears insignificant suggesting minimal risk to other intra-articular and per-articular tissues.

Example B: PDT Using Photofrin ® for the Treatment of Arthritis

Methods

Photochemotherapeutic synovectomy was performed on an antigen induced arthritis (AIA) model in 12 New Zealand white rabbits in a double control study. After a six week sensitization period, the joints of all animals were challenged bilaterally with an injection of albumin suspended in Freund's adjuvant. After five days, eight animals received systemic injections of 2 mg/kg of Photophrin ® II. At 24 hours, four animals underwent bilateral arthrotomy procedures. The right knee joint of each was exposed to 100J/cm2 of 630 nm laser light over a 20 minute period. The left knees, not receiving the laser light application, served as controls. At 48 hours post HPD injection, an additional 4 animals underwent the identical operative procedures. Postoperatively, all animals were returned to their cages and allowed free movement. Four animals, serving as a second set of controls, did not undergo surgery or receive laser light treatment. At one month post treatment, animals were sacrificed, knee joint synovium was then harvested, fixed, and stained with H and E for pathological evaluation.

Results: Three of four control animals displayed acute bilateral synovial inflammation. One of the four control animals did not react to the antigen challenge and showed no inflammation on pathology. Two of four animals treated at 24 hours post injection demonstrated a marked decrease in synovial inflammation in the right knee relative to the left control. Two knees showed a qualitative difference between right and left. Healing was comparable to the seen in previous experimentation with radiation synovectomy. Of the animals treated at 48 hours post injection, one died in anesthesia, and one showed a decrease in inflammation in treatment relative to controls. These results are shown in FIGS. 1 and 2.

Example C: Use of BPD for PDT

New Zealand white rabbits weighing 3–4 kg were sensitized to ovalbumin according to the aforementioned antigen induced arthritis model protocol. 5–7 days post joint challenge, knee joints were observed to be inflammed. Animals were sedated with Rompum and Ketamine and received a continuous infusion of intravenous saline. A 20 guage angiocath was inserted percutaneously into the right knee joint of the animal via an anteromedial portal. A 600 μm quartz optical fiber, attached to a laser induced fluorescence system, was passed via the angiocath into the knee joint. The distal tip of the cleaved fiber was placed in gentle contact with the synovium overlying the fat pad in the anterior knee joint.

Laser induced fluorescence system. The output of a pulsed nitrogen laser (VSL-337ND Laser Science Inc., Cambridge, Mass.) was used to pump a dye laser (DLM 220, Laser Science, Inc., Cambridge, Mass.) containing rhodamine 610 dye (Exciton Chemical Co., Dayton, Ohio). The 610 nm excitation pulses were launched into a 600 μm core diameter fused silica optical fiber (Superguide-G, Fiberquide Industries, Stirling, N.J.) with a 5 mm focal length lens. After coupling, reflection and fiber losses the typical pulse energies incident on the tissue were approximately 10 μJ. Fluorescence from the tissue is passed back through the same optical fiber. The output of the fiber is optically coupled to a quartz fiber bundle which had a circular arrangements of fibers at the input. The fibers at the output end of the bundle were arranged linearly and served as a 0.1 mm by 2.5 mm entrance slit for the f/3.8, 0.275 m polychromator (Monospec 27, Anaspec, Acton, Mass.). A long pass filter (CS2-59, Swift Glass Co., Elmira, N.Y.) was inserted before the quartz fiber bundle to eliminate scattered laser light. Fluorescence for wavelengths between 300 and 800 nm was recorded using an intensified 1024 diode array controlled by a OMA III multichannel analyser (Princton Applied Research, Princeton, N.J.). The intensifier is gated with 100 nsec pulses centered around the 3 nsec laser pulse. The multichannel analyser allows the recording of a complete spectrum with each excitation pulse. Twenty spectra are collected and peak values at 690 nm averaged for each measurement. As the laser operates at 10 Hz, approximately 2 secs are needed to acquire each spectra.

Figure 4:
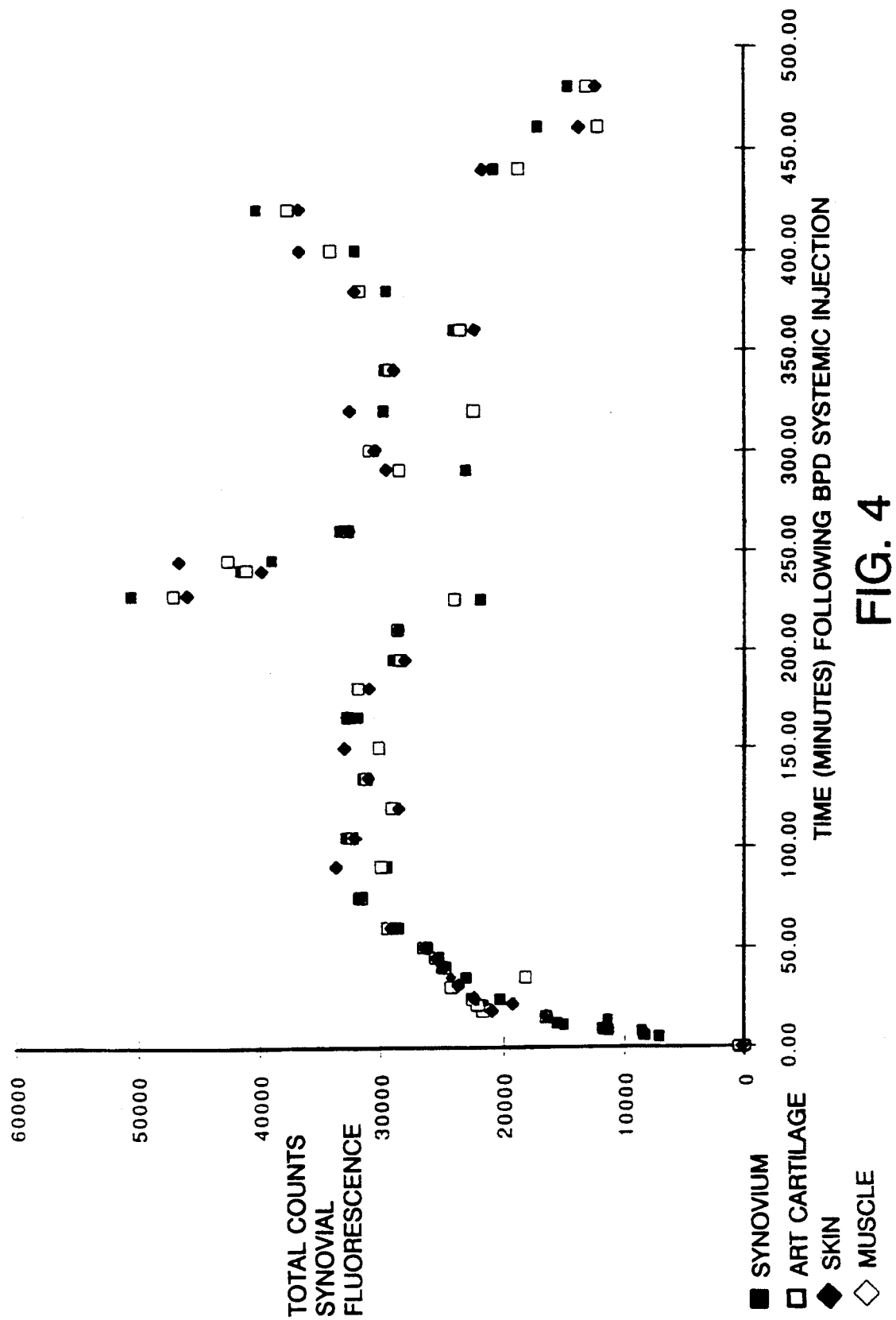
FIG. 4 is a graph of in vivo laser induced fluorescence of diseased synovial tissue following systemic administration of BPD.

Baseline values for fluorescence are recorded for synovium at 5 and 10 minutes prior to injection. The animal then receives a systemic injection of BPD. For the values in FIG. 4, the dose was 2 mg/kg. Recordings are then made in groups of 3 at progressive time intervals until 500 minutes. A plot of the recorded synovial fluorescence values vs time is seen in FIG. 4.

Example D: Use of ALA for PDT

Photodynamic therapy in which a precursor, δ-aminolevulinic acid (ALA), is administered and a synthesis of the photosensitizer is accomplished in situ. ALA is a precursor in the pathway of heme biosynthesis. The synthesis of ALA is the rate-limiting step in non-erythroid cells so that an increase of porphyrins is expected if this rate-limiting step is skipped by adding exogenous ALA to the cells. It is expected (see Table 4 below) that cells which grow faster may produce more porphyrin than slow growing cells. The use of ALA as the endogenous source of a PS in proliferative diseases such as rheumatoid arthritis is, therefore, promising.

Figure 5:
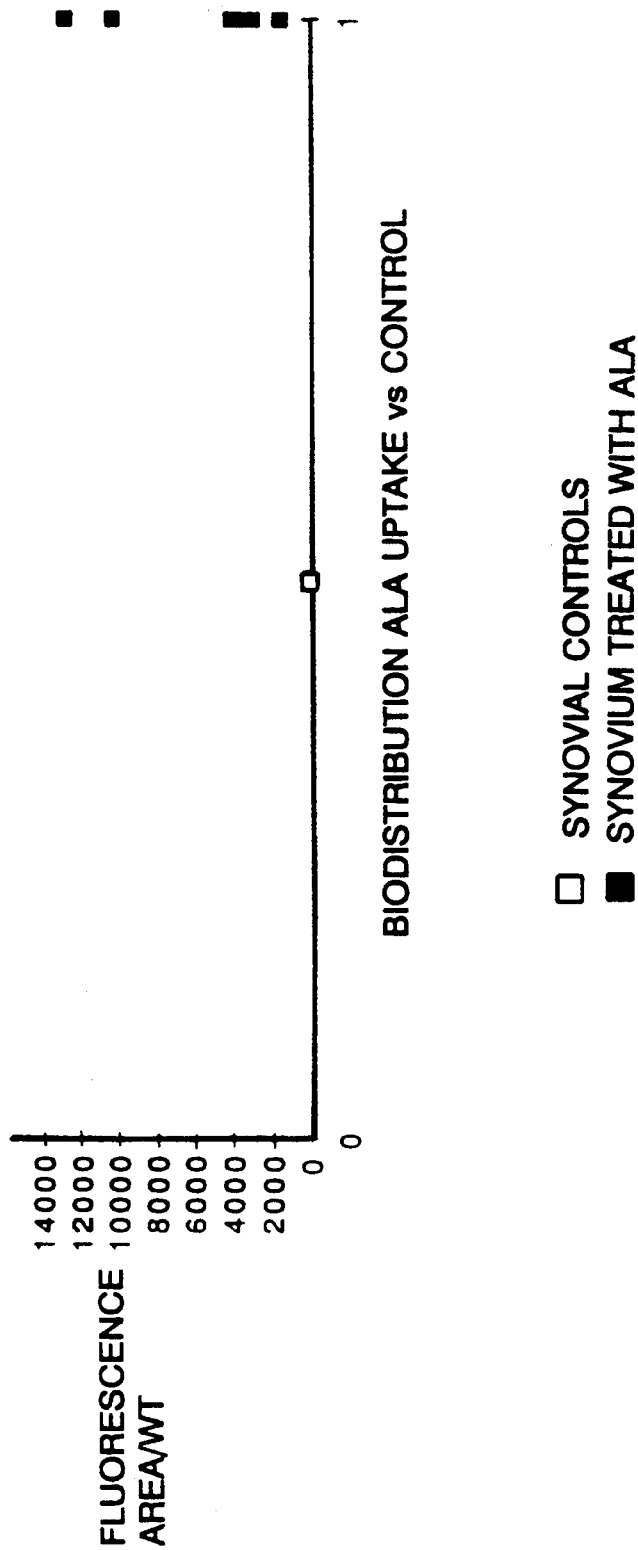
FIG. 5 is a graph of the localization of the precursor to protoporphyrin 1X, ALA, to the synovium.

Table 4 shows examples of PpIX synthesis and proliferative rates. We have demonstrated that cell-proliferation rates may in general be correlated to PpIX synthesis in cells. FIG. 5 shows the biodistribution of ALA in the antigen induced arthritis model. As can be seen by the open squares, in the absence of an injection no ALA is observed in the synovium. In contrast large amounts of ALA are observed in the synovium following injection.

TABLE 1

Diseases of the Joint Which May Be Treated with PDT

Rheumatoid Arthritis
Seronegative Spondyloarthropathies
Ankylosing Spondylitis
Seronegative Rheumatoid Arthritis
Psoriatic Arthritis
Juvenile Rheumatoid Arthritis
Reiter's Syndrome
Arthritis associated with Ulcerative Colitis
Whipple's Disease
Arthritis associated with Granulomatous Ileocolitis
Behcet's Disease
Systemic Lupus Erythematosus TABLE 1-continued Diseases of the Joint Which May Be Treated with PDT Sjören's Syndrome
Mixed Connective Tissue Disease
Hemophilia
Sickle Cell Disease and Trait
Arthritis Associated with Metabolic or Endocrine Disease
Arthritis Associated with Hemochromatosis
Arthritis Associated with Wilson's Disease
Arthritis Associated with Gaucher's Disease
Arthritis Associated with Alcaptonuria-Ochronosis
Arthritis Associated with Hyperlipoproteinemia
(Type II and Type IV)
Arthritis Associated with Multicentric Reticulohistocytosis
Arthritis Associated with Acromegaly, Hyperparathyroidism, and Hypoparathyroidism
Arthritis Associated with Hematologic Disease
Crystal-induced Arthrits: Pseudogout and Hydroxyapatite

TABLE 2

Compounds for Photodynamic Therapy of Diseases of the Joint

1. Photofril ®
2. Synthetic diporphyrins and dichlorins
3. Hydroporphyrins such as chlorins and bacteriochlorins of the tetra(hydroxyphenyl) porphyrin series
4. phthalocyanines
5. O-substituted tetraphenyl porphyrins (picket fence porphyrins)
6. 3,1-meso tetrakis (o-propionamido phenyl) porphyrin
7. Verdins
8. Purpurins
   tin and zinc derivatives of octaethylpurpurin (NT2)
   etiopurpurin (ET2)
9. Chlorins
   chlorin e6
   mono-l-aspartyl derivative of chlorin e6
10. Benzoporphyrin derivatives (BPD)
    benzoporphyrin monoacid derivatives
    tetracyanoethylene adducts of benzoporphyrin
    dimethyl acetylenedicarboxylate adducts of benzoporphyrin
    Diels-Adler adducts
    monoacid ring "a" derivative of benzoporphyrin
11. Low density lipoprotein mediated localization parameters similar to those observed with hematoporphyrin derivative (HPD)
12. sulfonation of aluminum PC as
    sulfonated AlPc
    disulfonated (AlPcS$_2$)
    tetrasulfonated derivative
    sulfonated aluminum naphthalocyanines
13. zinc naphthalocyanines
14. anthracenediones
15. anthrapyrazoles
16. aminoanthraquinone
17. phenoxazine dyes
18. phenothiazine derivatives
19. chalcogenapyrylium dyes
    cationic selena and tellurapyrylium derivatives
20. ring-substituted cationic PC
21. pheophorbide α
22. hematoporphyrin (HP)
23. protoporphyrin
24. 5-amino levulinic acid

TABLE 3

Schedule for Test Compounds

Group A: Experimental, 24 animals-- +
photosensitizer + light activation to
right knee, no light activation of left knee.

| | |
|---|---|
| Day 0 | Sensitize animals, skin injection |
| Day 30 | Sensitize animals, skin injection |
| Day 60 | Challenge joints with ovalbumin solution, create synovitis reaction |
| Day 66 | Systemic injection of the compound, treatment animals |
| Day 68 | Light activation of the compound via optical fiber, transillumination or open delivery via arthrotomy incision to the right knee of all 24 animals |

TABLE 3-continued

Schedule for Test Compounds

| Day 75 | Kill 6 treatment rabbits, harvest both knees |
| Day 83 | Kill 6 treatment rabbits, harvest both knees |
| Day 98 | Kill 6 treatment rabbits, harvest both knees |
| Day 148 | Kill 6 treatment animals, harvest both knees |
| | Group B: Control animals: no photosensitizer, light activation R knee, no light activation L knee |
| Day 0 | Sensitize animals, skin injection |
| Day 30 | Sensitize animals, skin injection |
| Day 60 | Challenge joints with ovalbumin solution, create synovitis reaction |
| Day 66 | Systemic injection of compound all animals |
| Day 68 | NO Light activation of compound |
| Day 75 | Kill 4 animals |
| Day 83 | Kill 4 animals |
| Day 98 | Kill 4 animals |
| Day 148 | Kill 4 animals |

TABLE 4

Cell Proliferation Rate Measured by Doubling Times (DTs)

| Cell Line | Dt (h) | Intracellular PpIX (4 h) (a moles/cell) |
|---|---|---|
| NBT-2 (rat bladder carcinoma) | 13.5 | 160 |
| 5PAM (murine squamous cell carcinoma) | 14 | 160 |
| EJ (human bladder carcinoma | 23 | 100 |
| HSF (human skin fibroblast) | 27 | 40 |

What is claimed is:

1. A method of treating a proliferative inflammatory joint disease in a patient, said method comprising
   a) administering to said patient a photoactivatable cytotoxic compound or precursor thereof so that said compound or precursor accumulates in synovial tissue of said patient, and then
   b) administering light of a photoactivating wavelength to said synovial tissue to activate said compound or precursor to cause destruction of said tissue.

2. The method of claim 1 wherein said photoactivatable compound is a benzoporphyrin derivative.

3. The method of claim 1 wherein said photoactivatable compound is a product of aminolevulinic acid.

4. The method of claim 1 wherein said compound is delivered systemically.

5. The method of claim 1 wherein said compound is delivered locally to the area of the joint.

6. The method of claim 1 wherein said light is administered directly to the joint.

7. The method of claim 6 wherein said administration is by an arthroscopic instrument.

8. The method of claim 6 wherein said administration is by a fiber optic instrument.

9. The method of claim 1 wherein said light is provided by a laser light source.

10. The method of claim 1 wherein said light is provided by a non-laser light source.

11. The method of claim 1 wherein said light is derived from a broad band light.

12. The method of claim 1 wherein said disease is an inflammatory arthritis disease.

13. The method of claim 12 wherein said disease is rheumatoid arthritis.

14. The method of claim 1 wherein said disease is hemophilia.

15. The method of claim 1 wherein said compound has a therapeutic index of at least 50.

16. The method of claim 1 wherein said compound has a therapeutic ratio of at least 10.

* * * * *